United States Patent [19]

Imran et al.

[11] Patent Number: 5,656,029
[45] Date of Patent: Aug. 12, 1997

[54] STEERABLE CATHETER WITH ADJUSTABLE BEND LOCATION AND/OR RADIUS AND METHOD

[75] Inventors: Mir A. Imran, Palo Alto; Mark L. Pomeranz, Los Gatos; Brian A. Glynn; Brett A. Follmer, both of Sunnyvale; Edward M. Gillis, Milpitas, all of Calif.

[73] Assignee: Cardiac Pathways Corporation, Sunnyvale, Calif.

[21] Appl. No.: 383,462

[22] Filed: Feb. 8, 1995

Related U.S. Application Data

[60] Division of Ser. No. 212,001, Mar. 11, 1994, Pat. No. 5,478,330, which is a continuation-in-part of Ser. No. 147,753, Nov. 5, 1993, Pat. No. 5,391,147, which is a continuation-in-part of Ser. No. 134,487, Oct. 12, 1993, Pat. No. 5,389,073, which is a continuation of Ser. No. 983,962, Dec. 1, 1992, abandoned.

[51] Int. Cl.⁶ .................................................. A61M 37/00
[52] U.S. Cl. ................................................ 604/95; 604/280
[58] Field of Search ................... 604/95, 280; 600/139, 600/146–152

[56] References Cited

U.S. PATENT DOCUMENTS

| 5,364,352 | 11/1994 | Crimino et al. | 604/95 |
| 5,397,321 | 3/1995 | Houser et al. | 606/41 |
| 5,487,757 | 1/1996 | Truckai et al. | 607/122 |
| 5,489,269 | 2/1996 | Aldrich et al. | 604/95 |
| 5,489,270 | 2/1996 | Van Erp | 604/95 |

*Primary Examiner*—Corrine M. McDermott
*Attorney, Agent, or Firm*—Flehr Hohbach Test Albritton & Herbert LLP

[57] ABSTRACT

A steerable catheter comprising a flexible elongate tubular member having proximal and distal extremities. A handle is secured to the proximal extremity. The tubular member has a lumen extending therethrough. A mandrel is slidably mounted in the lumen and extends into the distal extremity. A pull wire extends through the tubular member for causing bending of the distal extremity with respect to the mandrel disposed therein.

23 Claims, 6 Drawing Sheets

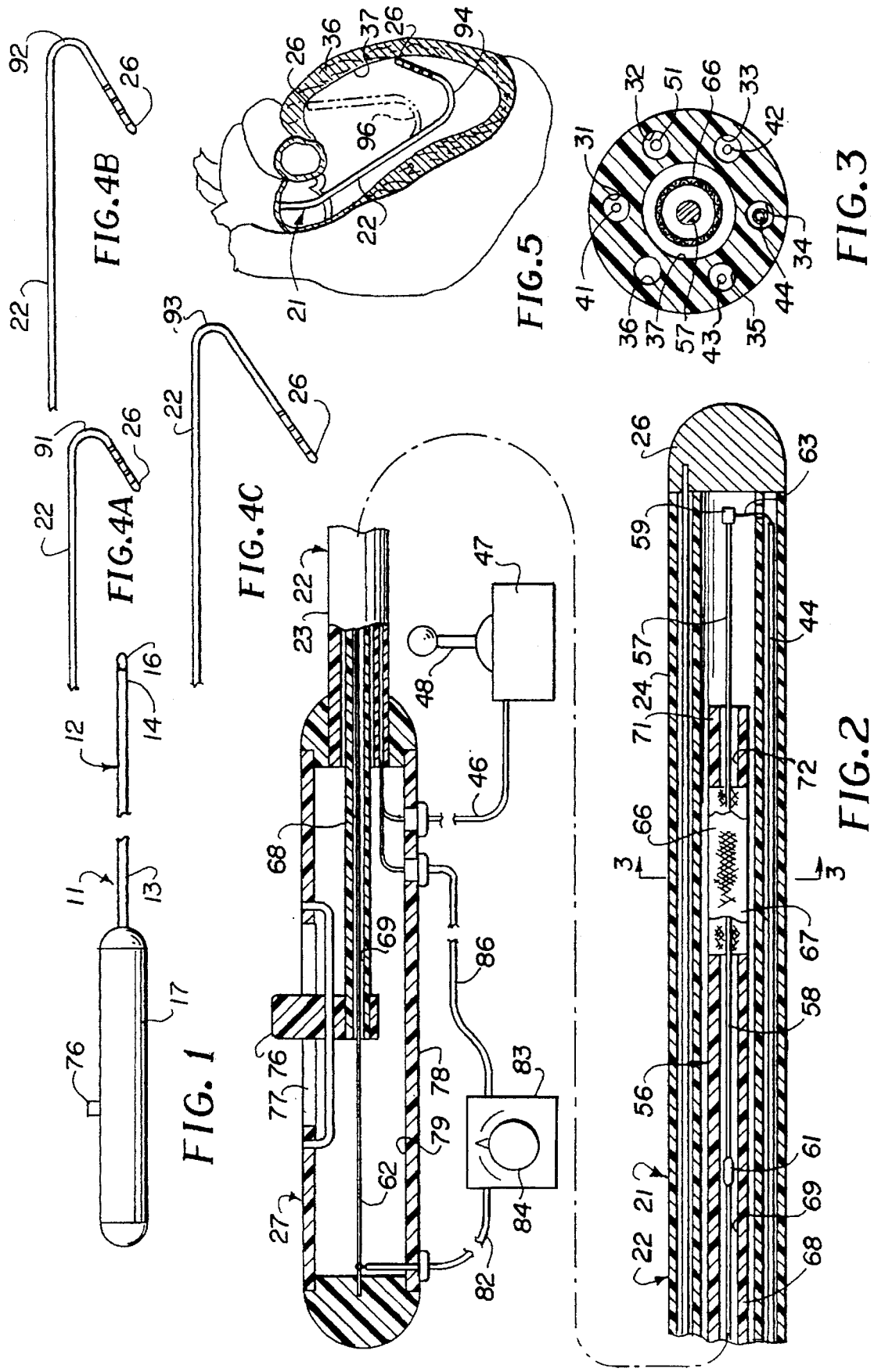

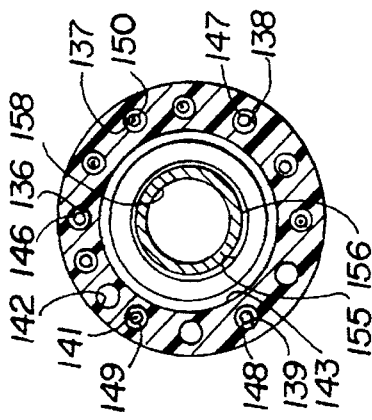
FIG. 10
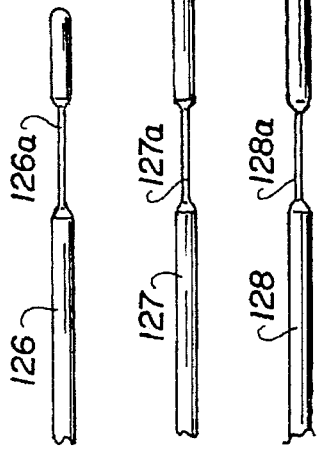
FIG. 8A
FIG. 8B
FIG. 8C
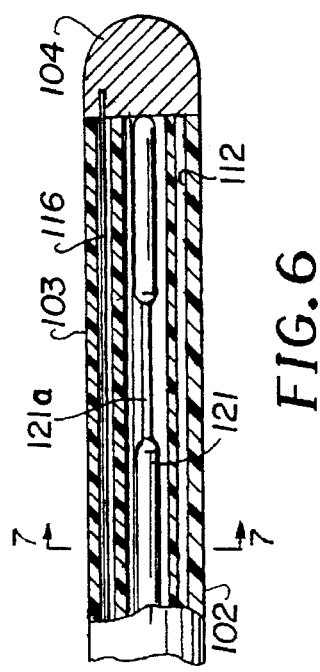
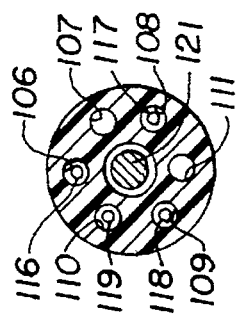
FIG. 6
FIG. 7
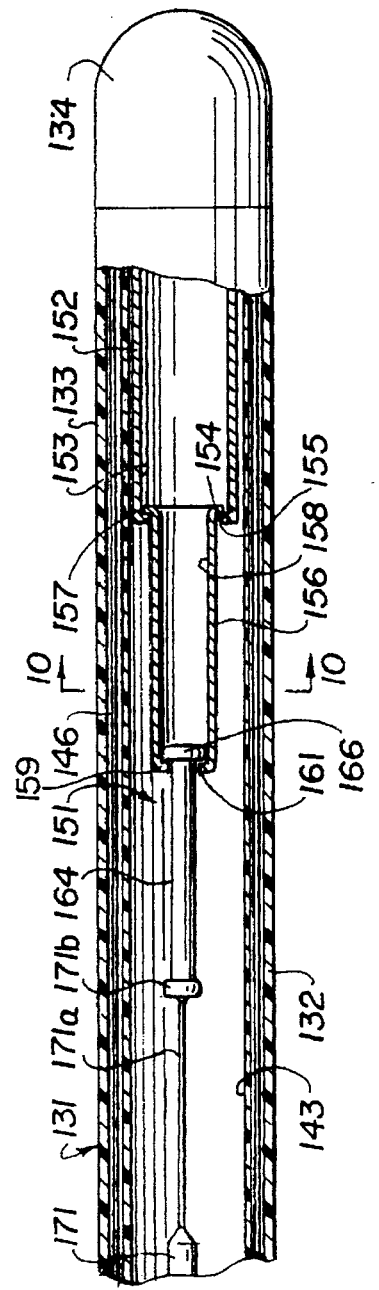
FIG. 9

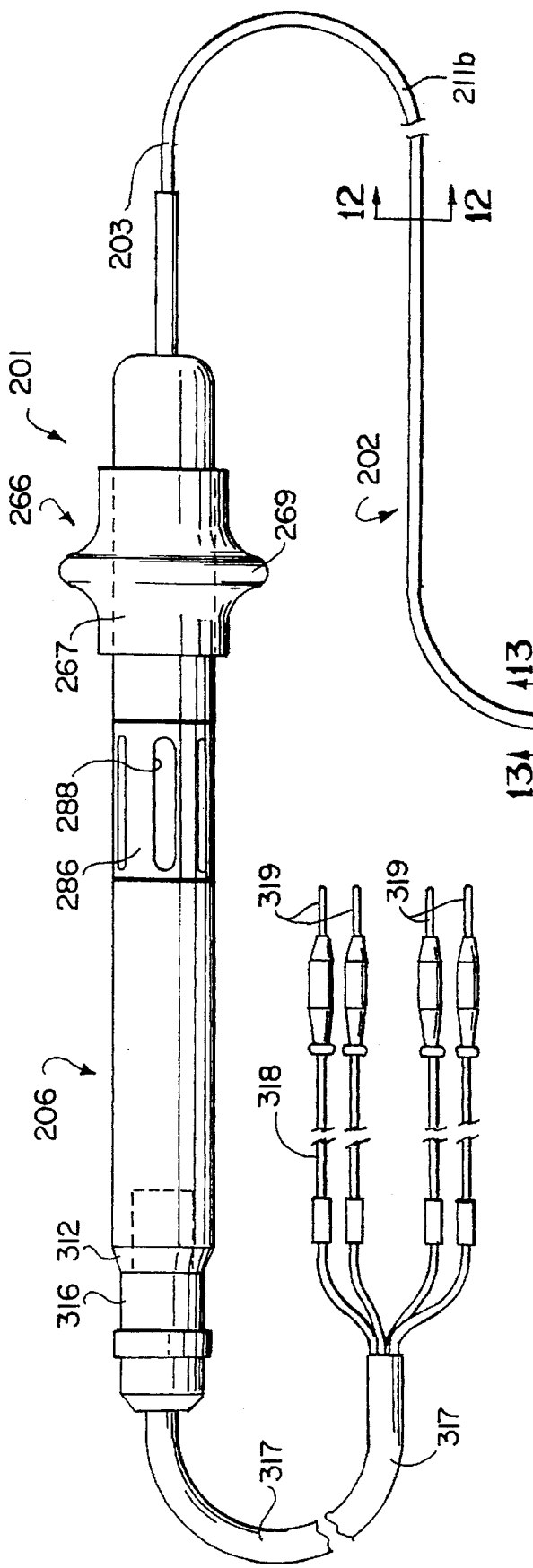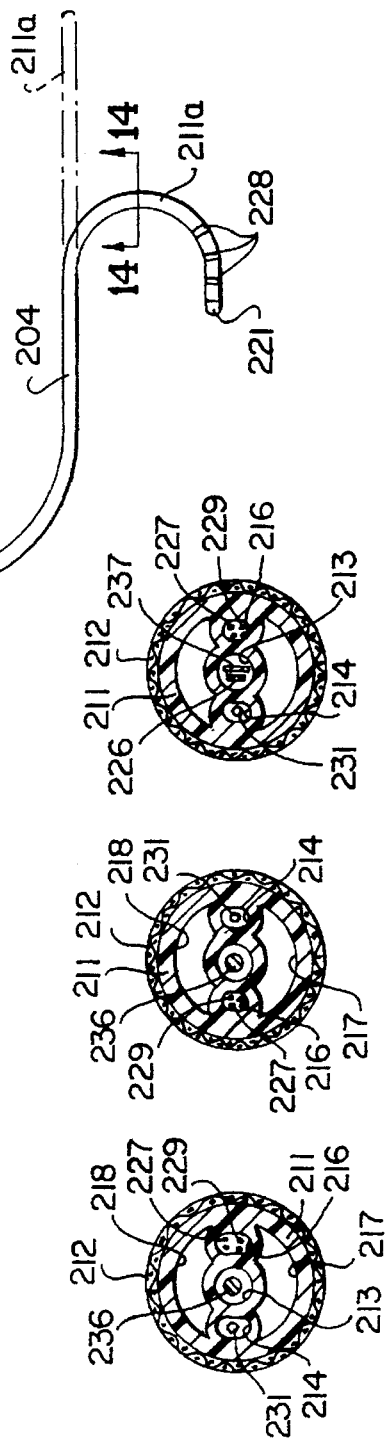
FIG. 11
FIG. 12
FIG. 13
FIG. 14

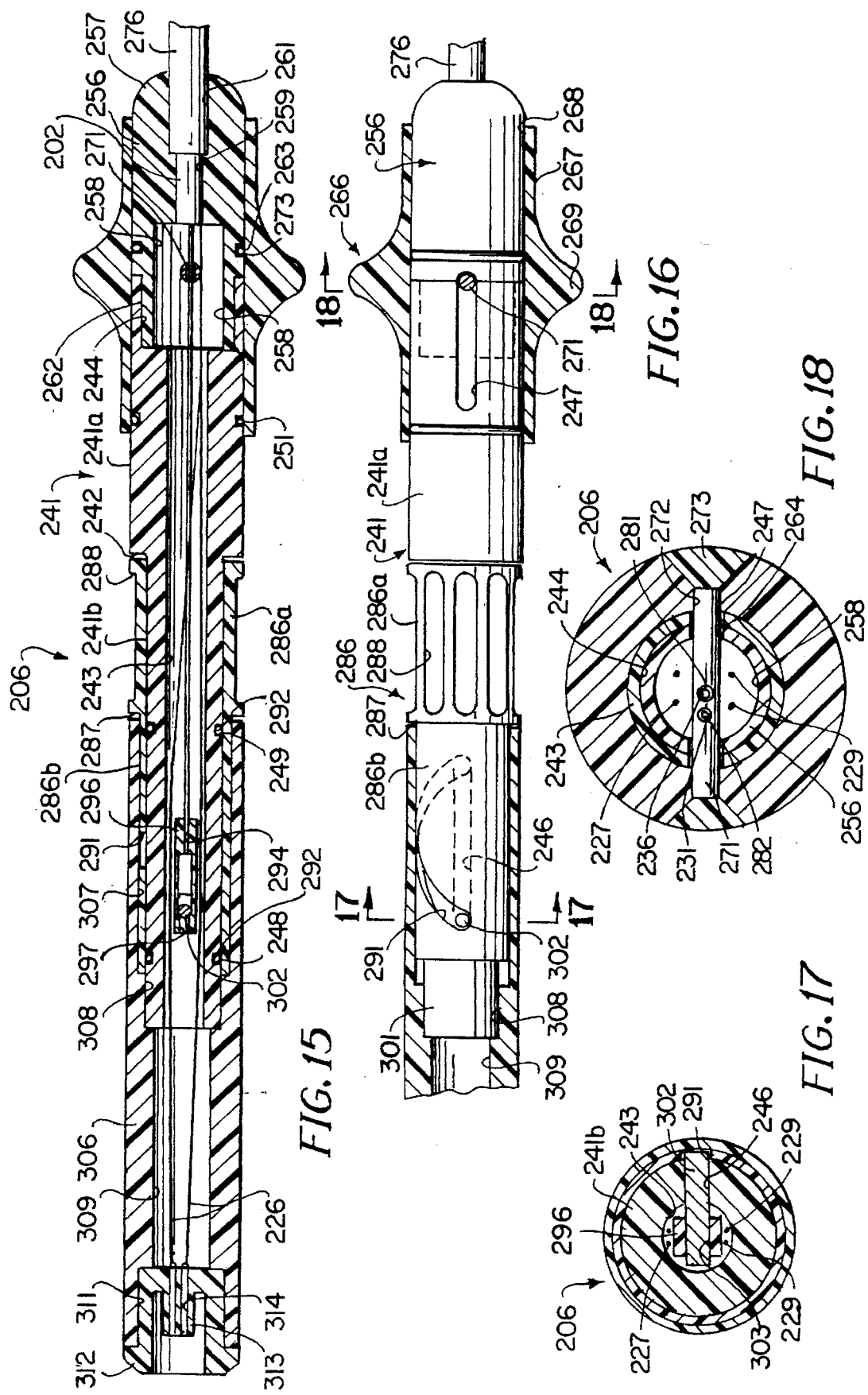

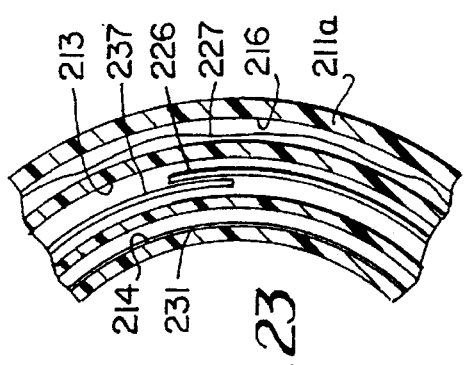
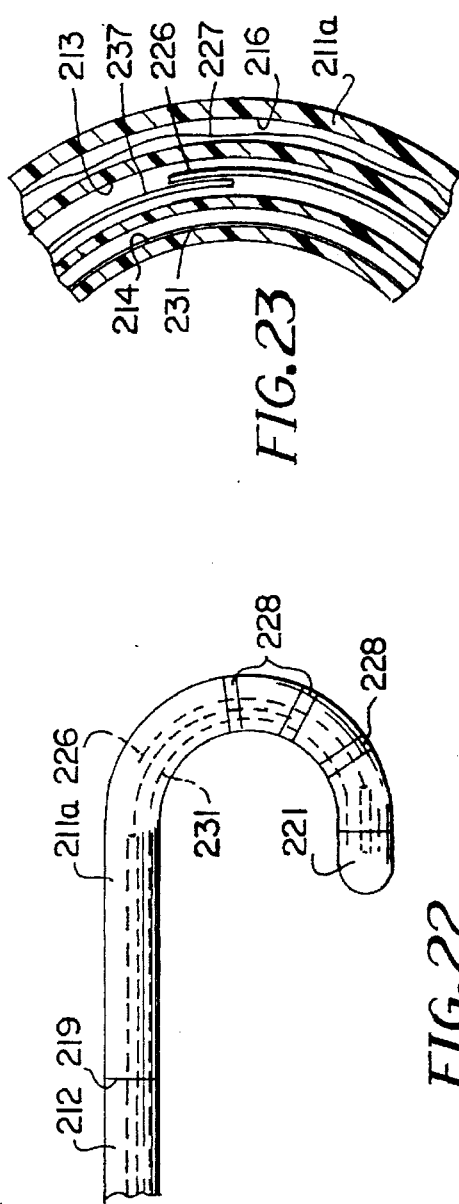
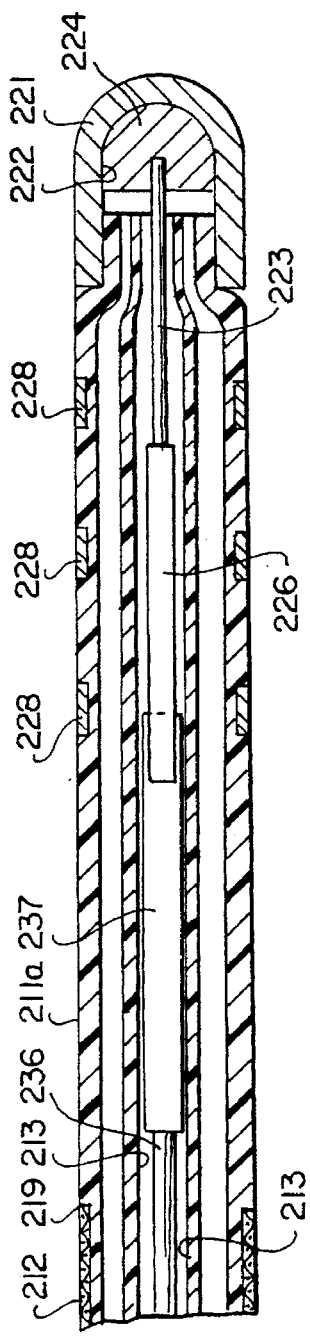
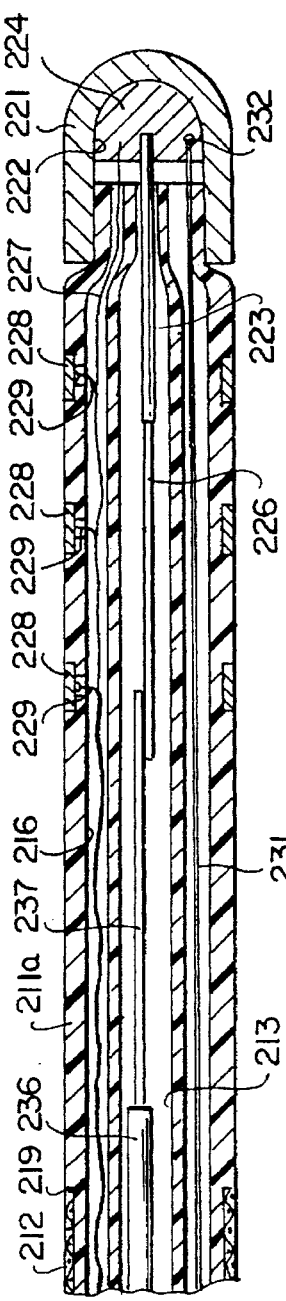
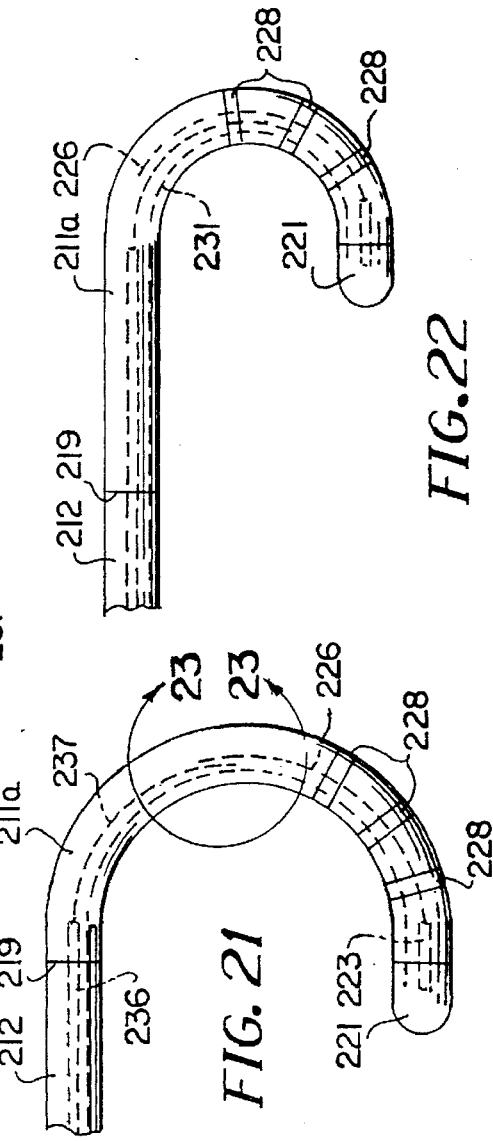

STEERABLE CATHETER WITH ADJUSTABLE BEND LOCATION AND/OR RADIUS AND METHOD

This is a division of application Ser. No. 08/212,001 filed Mar. 11, 1994 now U.S. Pat. No. 5,478,330, which is a continuation-in-part of application Ser. No. 08/147,753 filed Nov. 5, 1993 now U.S. Pat. No. 5,391,147 which is a continuation-in-part of application Ser. No. 08/134,487 filed Oct. 12, 1993 now U.S. Pat. No. 5,389,073, which is a continuation of application Ser. No. 07/983,962 filed Dec. 1, 1992 (abandoned).

This invention relates to a steerable catheter with an adjustable bend location and or bend radius and method.

In certain procedures, as for example ablation procedures for use with a steerable catheter in the human heart, it has been found that it is difficult to provide a bend in the appropriate location in the distal extremity of the steerable catheter while maintaining the rigidity of the distal extremity. This has found to be particularly true in patients having large hearts. Also it has been found that when the catheter shaft of the steerable catheter is inserted into the aorta of the heart, the distal extremity of the steerable catheter will exhibit a preference to be positioned with the deflected tip pointing in towards the arch which, when the proximal extremity of the steerable catheter is torqued will caused storing up and release of the energy as torquing continues to cause what is commonly known as whipping, which makes it difficult for the user of the steerable catheter to position the distal extremity of the steerable catheter. There is therefore a need for a new and improved steerable catheter which overcomes these difficulties.

In general, it is an object of the present invention to provide a steerable catheter with an adjustable bend location and method.

Another object of the invention is to provide a catheter and method of the above character in which whipping is eliminated.

Another object of the invention is to provide a catheter of the above character in which a build-up and release of energy is eliminated.

Another object of the invention is to provide a steerable catheter of the above character in which the distal extremity will rotate at a one-to-one relationship with respect to the proximal extremity of the catheter as the proximal extremity is rotated.

Another object of the invention is to provide a catheter and method of the above character which can be utilized with different types of bending mechanisms for the distal extremity of the catheter.

Another object of the invention is to provide a catheter and method of the above character in which the adjustment of the bend location can be readily accomplished.

Another object of the invention is to provide a catheter and method of the above character which is particularly adapted for use in mapping and ablation.

Another object of the invention is to provide a catheter and method of the above character in which the radius of the bend in the distal extremity can be changed while the catheter is in use.

Another object of the invention is to provide a catheter and method of the above character in which it is possible to adjust the length of the fixed portion of the distal extremity extending beyond the bend.

Another object of the invention is to provide a catheter and method of the above character in which the distal extremity of the catheter has been provided with less stiffness in a longitudinal direction to facilitate forming a bend in the distal extremity of the catheter and with additional stiffness in a lateral direction so that the distal extremity of the catheter can be maintained in engagement with the wall of the heart during beating of the heart.

Additional objects and features of the invention will appear from the following description in which the preferred embodiments are set forth in detail in conjunction with the accompanying drawings.

FIG. 1 is a side elevational view of a steerable catheter incorporating the present invention.

FIG. 2 is a side elevational view partially in cross-section showing one embodiment of a steerable catheter incorporating the present,invention utilizing a shape-memory element.

FIG. 3 is a cross-sectional view taken along the line 3—3 of FIG. 2.

FIGS. 4A, 4B and 4C show three examples of how an adjustable bend location in the steerable catheter makes possible bends in different locations in the distal extremity of the catheter.

FIG. 5 is a diagrammatic illustration showing the manner in which the steerable catheter of the present invention can be utilized in a human heart to provide a different bend location to make it possible to reach difficult-to-reach portions of the wall forming a chamber in the heart.

FIG. 6 is a partial cross-sectional view of another embodiment of a steerable catheter incorporating the present invention utilizing removable stiffening elements having weakened portions at different longitudinal positions of the stiffening elements.

FIG. 7 is a cross-sectional view taken along the line 7—7 of FIG. 6.

FIGS. 8A, 8B and 8C show stiffening elements having weakened regions in different longitudinal portions of the stiffening element.

FIG. 9 is a partial cross-sectional view of the distal extremity of another embodiment of a steerable catheter incorporating the present invention utilizing telescoping stiffening elements.

FIG. 10 is a cross-sectional view taken along the line 10—10 of FIG. 9.

FIG. 11 is a side elevational view of another embodiment of a steerable catheter incorporating the present invention.

FIG. 12 is a cross-sectional view taken along line 12—12 of FIG. 11.

FIG. 13 is a cross-sectional view taken along line 13—13 of FIG. 11.

FIG. 14 is a cross-sectional view taken along line 14—14 of FIG. 11.

FIG. 15 is an enlarged cross-sectional view of the handle of the steerable catheter shown in FIG. 11.

FIG. 16 is a cross-sectional view of a portion of the handle shown in FIG. 15 with certain portions being shown in cross-section and rotated by 90° from that shown in FIG. 15.

FIG. 17 is a cross-sectional view taken along line 17—17 of FIG. 16.

FIG. 18 is a cross-sectional view taken along line 18—18 of FIG. 16.

FIG. 19 is an enlarged cross-sectional view of the distal extremity of the catheter shown in FIG. 11.

FIG. 20 is a cross-sectional view similar to FIG. 19 but rotated by 90°.

FIGS. 21 and 22 are cross-sectional views of the distal extremity of the catheter shown in FIG. 1 showing in partially schematic form the manner in which different radius bends can be achieved by different positions of the bend location mandrel.

FIG. 23 is an enlarged partial cross-sectional View of the distal extremity of the catheter encircled on FIG. 21 showing how bending is accomplished.

Figure 24:
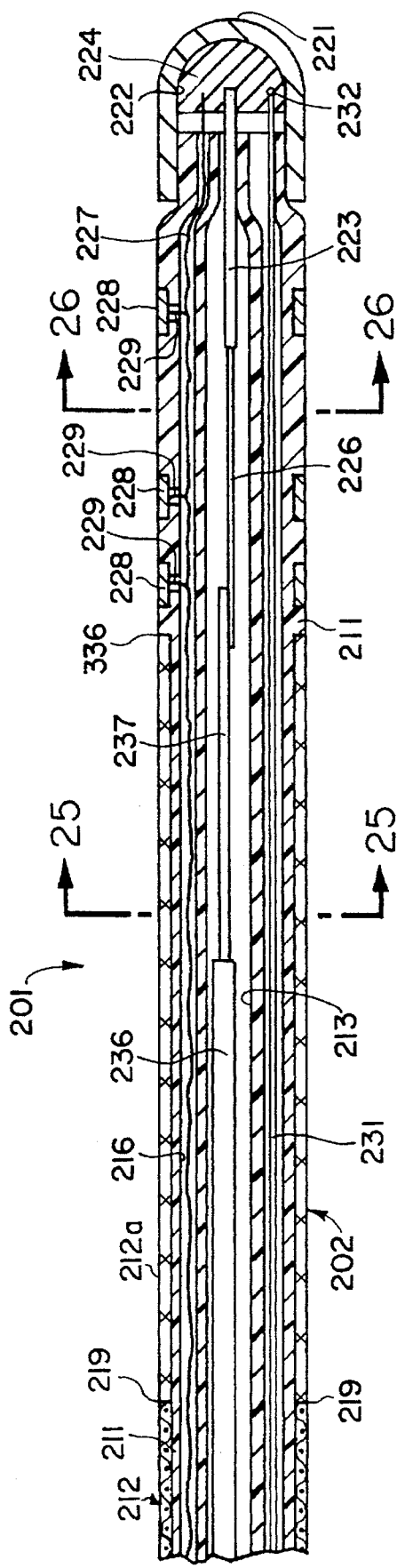
FIG. 24 is a cross-sectional view similar to FIG. 20 showing another embodiment of the present invention.

In general, the steerable catheter of the present invention consists of a flexible elongate tubular member having proximal and distal extremities. A plurality of circumferentially spaced-apart flexible elements are disposed in the distal extremity for causing bending of the distal extremity of the flexible elongate member. Movable means is disposed in the distal extremity of the flexible elongate member for selecting the location where bending in the distal extremity will take place and the radius of the bend.

More in particular, the steerable catheter 11 incorporating the present invention consists of a flexible elongate member 12 formed of a suitable material such as plastic which is provided with proximal and distal extremities 13 and 14. An ablation electrode 16 is carried by the distal extremity 14. A hand-held control mechanism 17 is mounted on the proximal extremity 13. The hand-held control mechanism 17 can be of various types. For example it can be of the type which can be utilized for actuating pull wires (not shown) extending longitudinally of the flexible elongate tubular member 12 which are well known to those skilled in the art and which can be utilized for bending the distal extremity of the flexible elongate tubular member 12. Alternatively, it can be provided with means for controlling flexible elongate elements having a negative coefficient of expansion disposed in the distal extremity 14 of the flexible elongate tubular member 12 as described in co-pending application Ser. No. 07/793,858, filed Nov. 18, 1991. Means not shown in FIG. 1 is provided for adjusting the bend location in the distal extremity of the flexible elongate tubular member 12 which will hereinafter be described in conjunction for specific embodiments of the present invention.

In FIGS. 2 and 3 there is disclosed a steerable catheter 21 which consists of a flexible elongate tubular member 22 which is provided with proximal and distal extremities 23 and 24. A metal ablation electrode 26 is secured to the distal extremity 24. A hand-held control mechanism 27 is mounted on the proximal extremity 23 of the flexible elongate tubular member 22. The flexible elongate tubular member 22 is formed of a suitable material such as plastic and is provided with a plurality of circumferentially spaced-apart lumens 31–36, and a central lumen 37, all of which extend the length of the flexible elongate tubular member 22. A plurality of flexible elongate elements, as for example three of such elements 41, 42 and 43, are disposed 120° apart and are provided in the lumens 31, 33 and 35. These flexible elongate elements 41, 42 and 43 are disposed in the distal extremity 24 of the flexible elongate tubular member 22 and are formed of a material which has a negative coefficient of expansion. The distal extremities of these flexible elongate members 41, 42 and 43 are connected to a common ground return 44 provided in the lumen 34. The three flexible elongate elements 41, 42 and 43 are also connected to conductors (not shown) which extend to the proximal extremity 23 of the flexible elongate member and with the ground return 44 connected into a cable 46 extending from the control mechanism 17 and are connected to a joystick control console 47 of the type described in co-pending application Ser. No. 07/793,858, filed Nov. 18, 1991, and which includes a joystick 48. The ablation electrode 26 is connected by a conductor 51 provided in the lumen 32 and extending into the control mechanism 17 and is connected to a suitable ablation power supply (not shown) conventionally used with such catheters.

Bend adjustment means 56 is provided in the distal extremity 24 of the flexible elongate tubular member 22 and consists of a shape-memory element 57 formed of a suitable material such as Nitinol which has been provided with a memory which makes it assume a straight condition when it is heated such as by the application of electrical energy thereto. The shape-memory element 57 is provided with proximal and distal extremities 58 and 59. The proximal extremity 58 is connected by a joint 61 to a conductor 62 which extends into the control mechanism and is connected as hereinafter described. The distal extremity 59 is connected to a ground return conductor 44 by wire 63. The shape-memory element 57 can have a suitable diameter, as for example 5–20 mils. The bend adjustment means 56 also includes selective conductive bypass means 66 which is movable longitudinally along the length of the shape-memory element 57 to selectively inhibit current flow in a portion of the shape-memory element to permit bending of the shape-memory element 57 in that portion of the shape-memory element.

The conductive bypass means 66 as shown in FIGS. 2 and 3 consists of an elongate cylindrical sleeve 67 formed of a suitable conducting material, as for example a silver mesh or braid, through which the shape-memory element 57 extends. Means is provided for adjusting the sleeve 67 longitudinally over the shape-memory element 57 and consists of a flexible tubular member 68 formed of a suitable insulating material such as plastic which is slidably mounted in the central lumen 37. The tubular member 68 is provided with a bore 69 therein extending the length thereof and in which the shape-memory element 57 is disposed. As can be seen particularly in FIG. 2, the sleeve 67 has one end secured to the distal extremity of the flexible tubular member 68. The other end of the sleeve 67 is supported by another tubular member 71 of the same material and of the same diameter as the flexible tubular member 68 and is provided with a bore 72 through which the shape-memory element 57 extends. The sleeve 67 can be affixed to the tubular members 68 and 71 by suitable means such as an adhesive.

In order to ensure good conductivity between the silver braid or mesh sleeve 67, the shape-memory element should be cleaned with nitric and hydrochloric acids to remove any oxidation which may be present on the shape-memory element 57. This ensures that there is good electrical contact between the sleeve 67 and the shape-memory element so that minimal or no current flows in the portion of the shape-memory element 57 which is covered by the sleeve.

Means is provided for controlling the movement of the flexible tubular member 68 and the sleeve 67 carried thereby from the control mechanism 27 and consists of a control member 76 which is secured to the proximal extremity of the tubular member 68. The control member 73 extends diametrically of the tubular member 68 through a longitudinally extending slot 77 provided in the sidewall of a cylindrical housing 78. The cylindrical housing 78 can be formed of a suitable material such as plastic or metal, and is sized in such a manner so that it is adapted to be held by the human hand. For example, it can have a diameter of approximately 1" and a length of 5–6". It is provided with a cylindrical recess 79 therein permitting the control member 76 with the attached flexible tubular member 68 to move therein relative to the conductor 62 which is mounted in an end cap 81 secured to the proximal extremity of the housing 78. The conductor 62 is connected to a cable 82 which extends out of the housing 78 and is connected to a variable current power supply 83 which is provided with a control knob 84 to adjust the amount of current which is supplied to the sleeve 67. The variable current power supply 83 is also provided with another cable 86 which is connected to the ground return conductor 44.

Operation and use of the steerable catheter 21 may now be briefly described as follows. Let is be assumed that it is desired to form a bend in the distal extremities 24 of the flexible elongate tubular member 22 in the position where the sleeve 67 has been located by movement of the control member 76. Current is supplied under the control of the control knob 84 from the variable current power supply 83 to the shape-memory element 57. The shape-memory element 57, when it is supplied with electrical energy, attempts to return to its memorized condition which, as pointed out before, is a straight condition. At the same time, it becomes stiffer. The conductive sleeve 67 however permits the portion of the shape-memory element 57 covered by the sleeve to remain flexible. This occurs because the sleeve 67, which is in close intimate contact with the shape-memory element 57, serves as a current bypass or bridge and causes the current to flow through the highly conductive silver mesh sleeve 67 to thereby bridge that portion of the shape-memory element 57 covered thereby so that it remains relatively flexible. Thus, the portion of the shape-memory element 57 underlying or within the sleeve 67 does not heat up and remains flexible and does not attempt to assume the straight condition of the remainder of the shape-memory element 57. By adjusting the longitudinal position of the sleeve with respect to the shape-memory element 57, it is possible to adjust the location at which the shape-memory element 57 will be flexible to permit bending at different locations so that shorter or longer straight or stiff portions can be provided at the distal extremity of the catheter 11 beyond the bend. Examples of such different locations of bends is shown by the bends 91, 92 and 93 in FIGS. 4A, 4B and 4C, respectively which show progressively longer stiff portions extending distally beyond the bends. FIG. 5 shows by providing different bend locations for the steerable catheter 11, it is possible to reach difficult-to-reach positions in the human heart. Two different bends represented by the bends 94 and 96 in the catheter 11 are shown in which the bend 96 in contradistinction to the bend 94 makes it possible to reach a difficult-to-reach area of the wall 96 forming the chamber 97 of the human heart 98.

Another embodiment of a steerable catheter incorporating the present invention is shown in the catheter 101 in FIGS. 6 and 7 which consists of a flexible elongate tubular member 102 formed of a suitable material such as plastic which is provided with a distal extremity 103 having a metal electrode 104 provided thereon. The flexible elongate member 102 is provided with a plurality of circumferentially spaced-apart lumens 106–111 and a central lumen 112. At least three pull wires 116, 117 and 118 are provided in the lumens 106, 108 and 109, which are connected into the distal extremity and which extend to the proximal end of the catheter 101 and are controlled by a conventional control mechanism (not shown) for causing bending of the distal extremity of the tubular elongate member 102. A conductor 119 is provided in the lumen 110 and is connected to the electrode 104. An elongate stiffening element 121 is slidably mounted in the central lumen 112. This stiffening element 121 is provided with a weakened longitudinal portion 121a of the stiffening element 121. This weakened portion 121a can be of a suitable length, as for example 1–5 cm. It can be seen that by utilizing such a stiffening element with such a weakened portion that the bending of the distal extremity 103 of the flexible elongate tubular member 102 will occur in the region of the weakened portion 121a.

In the event that it is desirable to provide a bend which has a longer stiffer portion extending beyond the bend, the stiffener element 121 can be interchanged with other stiffener elements, as for example stiffener elements 126, 127 and 128, as shown in FIGS. 8A, 8B and 8C, having weakened longitudinal portions 126a, 127a and 128a, respectively, at different longitudinal positions of the stiffener elements 126, 127 and 128. It can be seen that by selecting an appropriate stiffener element that the bend in the distal extremity of the flexible elongate member 102 can be made to occur in the desired location to provide different hinge points and also to provide different lengths of the stiffener element extending beyond the weakened region or hinge point.

Another embodiment of a steerable catheter incorporating the present invention is shown in the steerable catheter 131 depicted in FIGS. 9 and 10. As shown therein, the catheter 131 consists of a flexible elongate member 132 formed of a suitable material such as plastic which is provided with a distal extremity 133 to which there is secured a tip electrode 134. The flexible elongate member 132 is provided with a plurality of circumferentially spaced-apart lumens 137,138,139,141 and 142 and a central lumen 143. At least three flexible elongate elements 146, 147 and 148 are disposed in the lumens 136, 138 and 139 and are formed of a material having a negative coefficient of expansion. Their distal extremities are connected to a common ground return conductor 149 provided in the lumen 141. A conductor 150 is provided in the lumen 137 and is connected to the electrode 134. The flexible elongate elements 146, 147 and 148 are connected to a joystick-type of control hereinbefore described in connection with the embodiment as shown in FIG. 2, and for that reason is not shown in FIGS. 9 and 10.

The means for adjusting the bend location for the bending of the distal extremity 133 of the flexible elongate tubular member 132 is in the form of a telescoping assembly 151 formed of a suitable material such as stainless steel mounted in the central lumen of the distal extremity 133 of the catheter 131. The telescoping assembly 151 is movable between collapsed and extended positions and consists of an outer cylindrical member 152 which is secured within the distal extremity 133 by suitable means such as an adhesive. The outer cylindrical member is provided with a cylindrical bore 153 and a swaged end 154 providing an opening 155 in communication with the bore 153. An intermediate cylindrical member 156 is slidably mounted within the outer cylindrical member 152 and is provided with a flanged end 157 which is adapted to engage the swaged end 154 of the outer cylindrical member 152. The intermediate cylindrical member 156 is provided with a bore 158 and has a swaged end 159 forming a hole 161 extending therethrough. An inner cylindrical member 164 is provided which has a flange 166 which is adapted to travel in the bore 158. The inner cylindrical member 164 travels through the hole 161 and forms the distal extremity of an elongate flexible push-pull element 171 which extends to the proximal extremity (not shown) of the flexible elongate member 132. The flexible elongate element 171 can be formed of a suitable material such as stainless steel and can have a diameter of 0.012–0.025". It is provided a portion 171a of reduced diameter in close proximity to the inner cylindrical member 164 as shown in FIG. 9. By way of example, it can have a reduced diameter ranging from 0.006" to 0.015". The diameter of the flexible elongate element 171 should be of a diameter which is slightly greater than the size of the hole 161 for a purpose hereinafter described.

In utilizing the steerable catheter 131 shown in FIG. 9, the hinge point or bend location for the distal extremity 133 of the flexible elongate element 132 can be readily adjusted. For example, for the shortest possible stiff or straight length extending beyond the bend, the telescoping assembly 151 is in a collapsed position in which the push-pull element 171 has been pushed towards the distal extremity so that an enlarged portion 1 of the flexible elongate member 171 is in engagement with the proximal extremity of the intermediate cylindrical member 156 and the intermediate cylindrical member 164 is disposed entirely within the outer cylindrical member 132. To increase the length of this stiff portion extending beyond the bend, it is merely necessary to withdraw proximally the flexible elongate element 171 which will first pull the inner cylindrical member 164 proximally to increase the length of the stiff portion extending beyond the bend provided by the region 171a. To provide a still longer stiff portion extending beyond the bend, it is merely necessary to pull proximally the flexible elongate member 171 to cause the intermediate cylindrical member 156 to be pulled out of the outer cylindrical member 152 to thereby increase the length of the telescoping assembly 151 and to also increase the length of the stiff portion extending beyond the bend or hinge point 171a. Thus, it can be seen that by use of the telescoping assembly 151 and by pushing or pulling on the flexible elongate element 171 it is possible to adjust the length of the telescoping assembly and to thereby adjust the length of the stiff portion extending beyond the bend.

Another embodiment of the steerable catheter of the present invention having an adjustable bend location and/or radius is shown in FIGS. 11–20. The steerable catheter 201 consists of a flexible elongate member 202 having proximal and distal extremities 203 and 204. The proximal extremity 203 is secured to the handle 206 in the form of a control mechanism which is adapted to be grasped by the human hand.

The flexible elongate member 202 is comprised of a first or inner shaft 211 and a second or outer shaft or sleeve 212 coaxially mounted on the first or inner shaft 211. The inner shaft 211 is in the form of a plastic extrusion which has been provided with a plurality of lumens extending therethrough. The inner shaft 211 is formed in two portions 211a and 211b. Both portions can be formed of the same plastic material, as for example PEBAX manufactured by Atochem, Inc. of Glen Rock, N.J. However, in accordance with the present invention it is desirable to form the portion 211a of a softer material such as PEBAX having a 35 Shore D hardness and portion 211b of a harder material, as for example PEBAX having a 72 Shore D hardness. The portion 211b has a smaller outer diameter than the portion 211a to accommodate the second or outer shaft or sleeve 212 and to provide a smooth outer surface for the flexible elongate member 202. The two portions 211a and 211b can be readily joined together by a heat fusing process since both portions are formed of a PEBAX material.

The two portions 211a and 211b of the first or inner shaft 211 are provided with a centrally disposed lumen 213 extending the length thereof and two additional lumens 214 and 216 aligned diametrically with lumen 213 and extending the length of the shaft 211. Two additional crescent or moon-shaped lumens 217 and 218 are provided in the shaft 211 on opposite sides of the diametrically aligned lumens 213, 214, and 216.

The second or outer shaft or sleeve 212 is formed of a braided PEBAX material which has a braid embedded therein formed of a suitable material such as sixteen 40-gauge stainless steel strands having a braid angle of 60°. The second or outer shaft or sleeve 212 can have a suitable wall thickness, as for example 0.020" with a corresponding reduction in the diameter of the portion 211b with respect to the portion 211a so that the outer surface of the sleeve is flush with the outer surface of the portion 211a. The braided sleeve or shaft 212 stops short of the distal extremity of the flexible elongate member 202 as indicated by the line 219 (see FIG. 19).

The second or outer shaft or sleeve 212 serves to provide good torque transfer characteristics for the flexible elongate member 202. In order to prevent whipping of the distal extremity of the flexible elongate member 202 as the handle 206 is rotated, the portion 211a of the first inner shaft 211 has its distal extremity rotated or twisted through an angle, as for example from 270° to 250° and preferably approximately 360° through a length ranging from 10"–20" and preferably a distance of about approximately 15". FIG. 12 shows the initial starting position for the twist of the inner shaft portion 211a. FIG. 13 shows that the twist of the shaft portion 211a after it has been twisted by 180° and FIG. 14 shows the final twist of the shaft portion 211a after it has been twisted through 360°. This rotation of the distal extremity of the shaft portion 211a is retained in the flexible elongate member 202 by affixing the sleeve 212 at a suitable distance as for example 18" from the distal extremity of the flexible elongate member 202 as represented by the cross-section of FIG. 12 by suitable means such as heat staking and similarly approximately 3" from the distal extremity as represented by the cross-section in FIG. 14 by additional heat staking so that the 360 degree twist or turn hereinbefore described that occurs between 18" and the latter 3" of the distal extremity of the flexible elongate member 202 is retained therein by the forces of the braided outer sleeve 212.

A tip electrode 221 is mounted on the distal extremity of the portion 211a and is formed of a suitable material such as platinum and is formed as a deep drawn cup with a rounded distal extremity and having an outer circumference which corresponds to the outer circumference of the portion 211a. The tip electrode 221 can have a suitable diameter, as for example 0.091" and a have a suitable length, as for example 4 millimeters. The tip electrode 221 is provided with a longitudinal extending cavity 222. The distal extremity of the portion 211a is necked down and inserted into the cavity 222 and is retained therein by suitable means such as an adhesive (not shown). The tip electrode 221 is also secured to the distal extremity of the portion 211a by a member 223 in the form of a stainless steel hypotube having an outside diameter of approximately 0.025" and an inside diameter of 0.019" and having a length of approximately ¼" which is retained within the cavity 222 by a suitable means such as solder 224. The members 223 are secured to one end of a ribbon 226 by suitable means such as welding the ribbon 226 is formed of a suitable material such as a superelastic Nitinol which has a programmed memory of a straight shape. It can have suitable dimensions, as for example a width of 0.018" and a thickness of 0.006" and a length of approximately 3". The ribbon 226 is slidably disposed in the central lumen 213.

Means is provided for forming an electrical connection to the tip electrode 221 and consists of a insulated conductor 227 which has one end electrically connected to the tip 221 by the solder 224. The conductor 227 extends through the lumen 216 through the proximal extremity of the flexible elongate member 202.

A plurality of conductive rings 228 formed of a suitable material such as platinum are mounted in insulated spaced-apart positions on the portion 211a the shaft 211 and are connected to insulated conductors 229 which also extend to the proximal extremity of the flexible elongate member 202 through the lumen 216.

Means is provided for causing bending of the distal extremity of the flexible elongate member 202 and consists of a pull wire 231 formed of a suitable material such as stainless steel having a diameter of 0.005".

The pull wire 231 is slidably mounted in the lumen 214 and is connected into the tip electrode 221 by having a beaded end 232 secured within the solder 224. In order to reduce friction with respect to the sliding movement of the pull wire 231 within the lumen 214, the pull wire is coated with Teflon (not shown).

A bend location mandrel 236 is slidably mounted in the central lumen 213. As shown, it can be circular in cross-section and can have a suitable diameter, as for example 0.017". It is formed of a suitable material such as Nitinol. The proximal extremity of the bend location mandrel 236 is secured within the handle 206 as hereinafter described. The distal extremity of the mandrel 236 is secured by welding to an elongate ribbon 237 which is rectangular in cross-section and which is disposed in the central lumen 213. The ribbon 237 also is formed of a superelastic Nitinol which is rectangular in cross-section and can have suitable dimensions such as 0.019" and a thickness of 0.008". The ribbon 237 has a memory which causes it to return to a straight position when it is free to move. The ribbon 237 is mounted on the mandrel 236 so that it flexes in a direction which is at right angles to the width of the ribbon to permit bending of the portion 211a of the shaft 211 in the direction in which it can be pulled by the pull wire 231 but inhibiting flexing in a direction which is at right angles to the plane formed by the width of the ribbon. As shown in FIG. 20 of the drawings, the ribbon 237 overlaps the ribbon 226 and is slidable longitudinally with respect to the ribbon 226 to adjust the bend location as hereinafter described.

The handle 206 is in the form of an assembly which includes an elongate cylindrical body 241 formed of a suitable material such as plastic which is formed of a distal extremity 241a of a larger diameter and a portion 241b of a reduced diameter to form a shoulder 242. The body 241 is provided with an axially extending bore 243 extending therethrough which opens into a larger bore 244 provided in the distal extremity of the body 241. The portion 241b of reduced diameter is provided with an elongate slot 246 extending longitudinally thereof parallel to the longitudinal axis of the body 241. The portion 241a of larger diameter is also provided with first and second diametrically opposed open-ended slots 247 which are open at their distal extremities because they extend through the distal extremity of the body portion 241a. The slots 247 extend longitudinally of the body 241 and are parallel to the axis of the body 241. As shown in FIG. 16, the slots 247 are positioned so that at least one is aligned with the slot 246 in the portion 241b. The portion 241b of reduced diameter is also provided with spaced-apart inner recesses 249 on the outer cylindrical surface thereof. The body portion 241a is also provided with an annular recess 251 opening through the outer surface thereof.

The handle 206 also includes a cylindrical nose piece 256 that has substantially the same outer diameter as the portion 241a of the body 241. It is provided with a rounded distal extremity 257. The nose piece 256 is provided with a large bore 258 in the proximal extremity of the same which opens into a smaller bore 259 which in turn opens into a slightly larger bore 261. The nose piece is provided with an annular recess 262 on the proximal extremity of its outer surface which is sized so that the proximal extremity of the nose piece 256 can be fit within the bore 244 provided in the body 241. The nose piece 256 is also provided with an annular recess 263 which is spaced distally from the recess 262.

The handle 206 includes a handle member in the form of a circular knob 266 which is slidably mounted on the body 241 and the nose piece 256 when the nose piece is assembled into the body 241. The handle member 266 is in the form of an elongate sleeve 267 which has a bore 268 extending there through which is sized so that a slip fit is formed between the sleeve 267 and the body portion 241a and the nose piece 256. The handle member 266 is provided with an outwardly and circumferentially extending waist 269 which is provided with a rounded contour to facilitate grasping of the same by fingers of the hand holding the handle as for example the thumb and forefinger.

Means is provided for securing the handle member 266 to the body portion 241a that consists of a cylindrical pin 271 formed of a suitable material such as stainless steel which extends through the waist 269 and extends through the slots 247 and 264 (see FIG. 18) which serves to limit the sliding movement of the handle member 266 to the length of the cooperating slots 247 and 264.

The nose piece 256 is provided with first and second diametrically opposed slots 264 which open through the proximal extremity of the nose piece 256 and are aligned with the slots 247 in the body 241 so that when the nose piece 257 is assembled into the body 241, the slots 264 close the open ended slots 247.

A pin 271 is disposed in counter-sunk bores 272 in the handle member which after the pin 271 is in place are filled with additional plastic 273 that is ground and polished so that the pin 271 is hidden from view of the human eye.

The proximal extremity 203 of the flexible elongate member 202 is disposed in the bore 259 in the nose piece 256 is retained therein by suitable means such as an adhesive (not shown). A strain relief sleeve 276 formed of a suitable material such as plastic is mounted in the bore 261 and is retained therein by suitable means such as an adhesive (not shown) and extends over the proximal extremity of the flexible elongate member 202 (see FIG. 11).

The bend location mandrel 236 extends from the proximal extremity of the flexible elongate member 202 and passes through a hole 281 provided in the pin (see FIG. 18). The pull wire 231 also extends from the proximal extremity of the flexible elongate member 202 into the handle 206 and extends through a hole 282 offset from the hole 281 (see FIG. 18).

The handle 206 also consists of the sleeve 286 which is provided with a portion 286a of a larger diameter handle and a portion 286b of a smaller diameter to form a shoulder 287. The portion 286a of larger diameter is provided with a plurality of circumferentially spaced apart longitudinally extending recesses 288 which are adapted to be grasped by the fingers of the hand holding the handle 206. The portion 286b is provided with a helically extending slot 291 which has its ends coterminus with the ends of the slot 246 in the portion 286b when the sleeve 286 is positioned over the portion 241b as shown in FIGS. 15 and 16. O-rings 292 provided in the annular recesses 248 and 249 and serve to provide a slight frictional engagement between the sleeve 286 and the body 241 to slightly inhibit the rotation of the sleeve 286 with respect to the body 241. The o-ring also prevents a fluid from entering the handle 206.

An O-ring 273 is provided in the recess 263 which serves to provide a slight frictional engagement to retain the handle member 266 in a desired position longitudinally of the body 241 while still permitting relatively free movement of the handle member 266 relative to the body 241.

The bend location mandrel 236 extends through the bore 243 of the body 241. The bend location mandrel 236 is formed of a suitable material such as 0.018" Nitinol wire. It extends through a bore 294 provided in a block 296 formed of a suitable material such as plastic. The bore 294 opens into a larger bore 297 in the block 296 which opens through the distal extremity of the block. A sleeve 301 formed of a suitable material such as stainless steel hypotube having an inside diameter of 0.020" and outside diameter of 0.032" is secured to the proximal extremity of the bend location mandrel 236 by suitable means such as a TIG weld. The sleeve 301 is disposed in the bore 297 and retains the proximal extremity of the bend location mandrel 236 within the block 296 which as shown in FIG. 17 can have a rectangular cross-section. The sleeve 301 with the bend location mandrel 236 is retained within the block 296 by a dowel pin 302 which extends through a bore 303 transversely of the block 296 immediately behind the sleeve 301 to retain the sleeve 301 in the bore 297. The pin 302 also extends through the elongate slot 246 provided in the body 241 and into the helical slot 291 whereby as the sleeve 286 is rotated, the pin 302 will be caused to translate longitudinally of the handle 206 in the slot 246 to advance and retract the bend location mandrel 236 for a purpose hereinafter described.

The handle 206 includes a cylindrical end piece 306 also formed of a suitable material such as plastic which is provided with a bore 307 opening through the distal extremity of the same. The bore 307 opens into a smaller bore 308 which in turn opens into a still smaller bore 309. The bore 309 opens into a larger bore 311 (see FIG. 15). When the end piece 306 is assembled on to the body 241 and retained thereon by suitable means such as an adhesive (not shown) the portion 286b is rotatably seated within the bore 307 whereas the portion 241b is secured in the bore 308. A plug 312 is seated within the bore 311 and is retained therein by suitable means such as an adhesive and carries a female electrical connector 313 of a conventional type which is recessed therein and which is provided with female recesses 314 formed of a conducting material which are connected to the conductors 226. A male connector 316 of a conventional type is adapted to seat within the female connector 313 (see FIG. 11) and is connected to a cable 317 that carries conductors 318 connected to conventional pins 319 that are adapted to be connected into conventional instrumentation for performing an ablation procedure as hereinafter described.

Operation and use of the steerable catheter 201 may now be briefly described as follows. Let it be assumed that it is desired to utilize the steerable catheter 201 in an ablation procedure in the heart of a patient. The distal extremity 204 of the flexible elongate member 202 of the steerable catheter 201 can be introduced into the vessel of the patient, as for example a femoral artery in a conventional manner and introduced into the heart of the patient to a desired chamber of the heart by steering the distal extremity 204 of the flexible elongate member 202. The advancement of the distal extremity 204 can be observed fluoroscopically. In accordance with the present invention, large radius and small radius bends may be provided in the distal extremity 204 to make it possible to negotiate the vessel leading to the heart and to enter appropriate pathways in the heart to position the distal extremity 204 in an appropriate position in the chamber of the heart to perform an ablation.

Let it be assumed that in introducing the distal extremity 204 into the vessel of the patient it is desired to have the distal extremity be straight as shown in dotted lines in FIG. 1. This is accomplished by the physician or surgeon grasping the handle 206 in one hand and utilizing the thumb and forefinger of the same hand to grasp the enlarged waist 269 to push the same distally of the handle 206 to cause pin 271 carried thereby to move distally of the handle and to carry with it the pull wire 231 to extend its proximal extremity distally to permit the proximal extremity 211a to straighten out under the force of the superelastic ribbons 226 and 237 which have a memory to urge them into a straight shape when they are free to move.

Let it also be assumed that the cylindrical knob provided by the sleeve 286 is in a position so that the dowel pin 302 is in the proximal extremity of the helical slot 291 as shown in FIG. 1 so that the bend location mandrel 236 has been retracted to its extreme proximal position. With the catheter in this condition, the portion 211a of the shaft 211 will be relatively soft and floppy so that it can readily negotiate the femoral artery or other vessel into which it is being introduced. As the distal extremity 204 is being advanced, a bend can be placed in the distal extremity 204 when desired to negotiate a tortuosity in the vessel. This can be readily accomplished by the hand gasping the circular knob 266 and progressively retracting the same to pull on the pull wire 231 to cause progressive bending of the distal extremity 204. The pull wire 231 hugs the inside margin of the lumen 214 (see FIG. 23) and causes bending in a direction perpendicularly to the plane of the ribbon. When the bend location mandrel 236 is in the retracted or proximal-most position, the radius of the bend created will be at a maximum radius as shown in FIG. 21, as for example 35 millimeters. If a smaller radius is desired, the bend location mandrel 236 can be advanced by rotation of the sleeve 286 to cause the distal extremity of the mandrel 236 and the ribbon 237 carried thereby to be advanced distally to progressively overlap the ribbon 226 to cause the radius of the bend to be decreased. Extending the mandrel 236 with the ribbon 237 carried thereby to its distal-most extremity it can create a bend having a radius as small as 18 millimeters as shown in FIG. 22. Thus it can be seen that the radius of the bend can be increased in connection of the present embodiment without substantially changing the position of the bend. In the previous embodiments hereinbefore described, the bend location was changed but the radius was kept relatively constant.

In the present invention the catheter 201 has its distal extremity 204 arranged in such a manner that it only bends in a single direction because of the orientation of the ribbons 237 and 238 so that bending can only occur in a direction which is perpendicular to the width of the ribbons 226 and 237. The direction of bending will only occur in one direction because the pull wire 231 is disposed on one side of the ribbons 236 and 237 so that the ribbons will be bent in a direction toward the pull wires 231. As this bending is created in the distal extremity 204, the distal extremity can be torqued through an angle 360 degrees and more by utilizing the hand holding the handle to rotate the handle 206 the desired amount. Because of the braided construction of the second or outer shaft or sleeve 212, there is a good torque transmission from the handle 206 through the proximal extremity of the flexible elongate member 202 to the distal extremity of portion 211a so that the distal extremity 204 will follow on a one-to-one relationship with respect to rotation of the handle 206. This one-on-one relation and torque transfer occurs even though the distal extremity of the flexible elongate member 202 passes over the aortic arch without whipping. This is made possible because the multilumen shaft 211 has been twisted through 360° as hereinbefore described within the braided or outer shaft or sleeve 212 so that the pull wire 231 shows no preferential orientation as it goes over the aortic arch. Because of the helix placed in the pull wire 231 by twisting of the portion 211a, the pull wire cannot assume a preferred orientation as it travels over the aortic arch. The approximately 15 centimeters of the flexible elongate member which is provided with this twist extends along the length of the portion of the catheter which typically would form the bend going over the aortic arch. Thus it can be seen, that the distal extremity 204 of the flexible elongate member 202 can be readily advanced into a chamber of the heart with bends in the heart being readily negotiated by placing the appropriate bend in the distal extremity and by selecting the appropriate radius for the bend. This can be readily accomplished by one hand of the physician holding the handle for rotation of the same and for creating bends of various radii by operation of the circular hob 266 and the sleeve hob 286. The distal extremity 204 can be readily advanced so that the tip electrode 221 and, if desired, the other spring electrodes 228 can be brought into engagement with the wall of the heart by appropriate operation of the handle 206. By utilizing the ribbons of superelastic Nitinol, it is possible to provide spring-like members which can be utilized to apply force to the wall of the heart while inhibiting sideways motion of the tip and thereby ensuring that the tip electrode will remain in contact with the wall of the heart eventhough the wall of the heart moves during beating of the heart. After the tip electrode has been appropriately positioned, radiofrequency energy can be supplied to the tip to create a lesion in the wall of the heart to perform the desired ablation. As disclosed in a co-pending application Ser. No. 07/983,732 filed Dec. 1, 1992 a cooling fluid that can be supplied to the tip electrode by round trip passage through the lumens 217 and 218.

After the ablation procedure has been completed, the bend in the distal extremity of the catheter can be removed by appropriate movement of the circular knob 266 and the sleeve knob 286 to permit removal of the steerable catheter 201 from the heart and then from the vessel of the patient.

In connection with the foregoing it can be seen that the steerable catheter 201 has several significant features. Because of the twisting of the catheter shaft 211, it is possible to avoid whipping of the catheter shaft and to prevent the pull wire from moving into a preferential position. The braided shaft or sleeve 212 serves two functions. It serves to prevent unwinding of the twist placed in the inner shaft 211. Also it makes it possible to transfer torque from one end of the outer shaft 212 to the other end of the shaft 212.

In connection with the construction which is shown in FIGS. 19–20 it should be appreciated that in place of the ribbon 226, a pair of Nitinol wires of a suitable diameter such as 0.010" can be welded together along their length to provide a flat member which corresponds essentially to the ribbon 226. The mandrel 236 can have such a length so it overlaps the wires.

Alternatively, in place of the member 233 secured in the solder 224 in the tip 221, a Nitinol ribbon can be soldered into the tip with the proximal extremity of the ribbon being connected to the pull wire 231. In this embodiment, the strip would have a memory which would preferentially cause it to seek a straight shape. Also alternatively, a Nitinol ribbon could be secured to the proximal extremity of the member 223 shown in FIG. 19 which also would have a memory which would cause it to assume a straight condition when permitted to do so. The mandrel 236 could extend distally so that it overlaps such a ribbon. In all of these embodiments it can be seen that a superelastic member has been provided with a memory of a straight shape so that when the pull wire is released, the distal extremity 202 of the flexible elongate member will assume a relatively straight shape so that it can be introduced into and removed from vessels in the patient.

Figure 25:
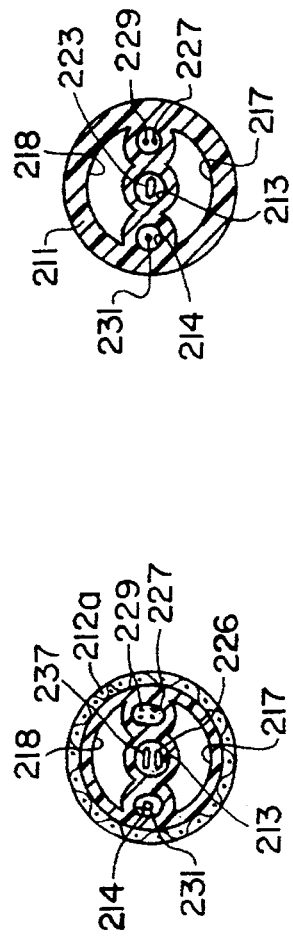
FIG. 25 is a cross-sectional view taken along the line 25—25 of FIG. 24.
Figure 26:
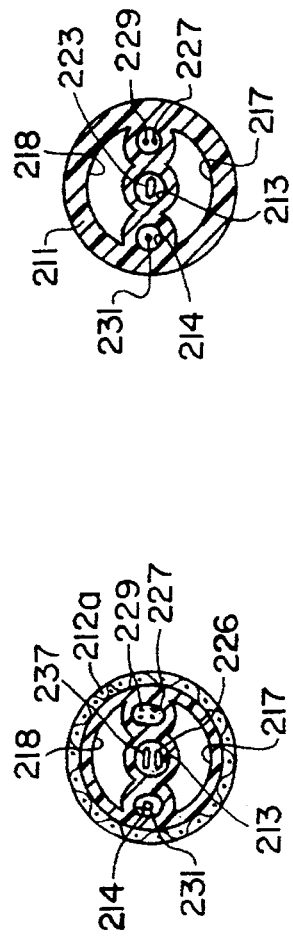
FIG. 26 is a cross-sectional view taken along the line 26—26 of FIG. 24.

Another embodiment of the invention is shown in FIGS. 24, 25, and 26 which is very similar to the embodiment shown in FIGS. 19 and 20 with, however, certain improvements made thereto to provide additional assurance that the distal extremity of the catheter 201 after a bend has additional transverse or lateral stiffness to help ensure that the tip electrode 221 as well as the conductive rings 228 remain in contact with the moving wall of the beating heart while still making it possible to more readily form bends in the distal extremity of the catheter. The construction making this possible is shown particularly in FIGS. 24, 25 and 26 and as shown therein consists of a second or outer shaft 212 which is provided with an additional braided portion 212a that extends from the line 219 at which the braided second or outer shaft 212 terminates and continues to a line 336 which is closely adjacent to the first of the conductive rings 228 provided in the distal extremity of the first or inner shaft 211. Byway of example, the flexible elongate member 202 can have a suitable length, as for example 85 centimeters whereas with the distal from which the portion 212a begins having a length of approximately 15 centimeters.

In order to impart the desired characteristics hereinbefore described for the catheter shown in FIGS. 24, 25 and 26, the portion 212a is formed of a lower durometer material than the portion 212. By way of example, the braided second or outer shaft 212 can be formed of shaft material such as PEBAX 7233 having a 72 D durometer and being impregnated with approximately 20% by weight of barium sulfate ($BaSO_4$). In contrast to this 72 D durometer hardness material, a softer material can be utilized which in accordance with the present invention should be at least 25% softer and as much as approximately 50% softer. Thus, this shaft material can be formed of PEBAX 3533 and also is filled with 20% by weight of barium sulfate. It should be appreciated if desired, the materials utilized for the shaft 212 and the distal extremity 212a can be formed of various durometer materials ranging from 35 D to 72 D Shore hardness. However, as pointed out above, in accordance with the present invention it is desirable that the hardness of the outer shaft portion 212a be at least 25% less than the hardness of the material utilized for the outer shaft 212. The braid utilized in the portion 212a can be very similar to that utilized in the portion 212. For example, the braid can be formed of a 304 stainless steel wire having a diameter of 0.003". Also byway of example it can be formed of 16 fillaments with a one over two configuration and a 60° braid angle.

The first or inner shaft 211 can be formed of a suitable shaft material such as PEBAX 5533 with a Shore hardness of 55 D and formed entirely of plastic with a 20% barium sulfate filler.

It has been found that the construction shown in FIGS. 24, 25 and 26 has a number of advantages. By providing the braid in the portion 212a with the shaft material being formed of a lesser Shore hardness material it is possible to provide a distal extremity in which a bend can be formed more easily while still providing improved lateral stiffness. Thus, when the distal extremity is formed into a bend so that the electrodes carried by the distal extremity can have additional springiness and be maintained in engagement with the wall of the heart while the heart is beating. In other words, the distal extremity is less floppy than the distal extremity in the embodiments hereinbefore described. The catheter 201 shown in FIGS. 24, 25 and 26 still has excellent torque transmission characteristics so that when the proximal extremity of the catheter is rotated the distal extremity will follow and can be maintained in contact with the wall of the heart to make it possible to supply radiofrequency energy to provide deep lesions in the wall of the heart.

In other words, the adding of the additional braided portion 212a has made it possible to increase the lateral stiffness of the tip of the catheter by making it possible for the physician or other person utilizing the catheter to torque the catheter into a position so that the tip 21 and the ring electrodes 228 can be brought firmly into engagement with the wall of the heart and be retained in engagement with the wall of a beating heart. In other words, the distal extremity of the catheter will hug the wall of the heart regardless of how the wall is moving during beating of the heart. This helps to ensure that a good lesion will be formed when RF energy is supplied to the tip electrode 221 and to the ring electrodes 228.

From the foregoing it can be seen that there have been provided a number of different embodiments of an invention in which it is possible to adjust the bend location and/or radius of the distal extremity of a steerable catheter while it is in use which makes it possible for the steerable catheter to be utilized to move its tip into many different locations, and particularly into locations which are difficult to reach with conventional steerable catheters. This is particularly advantageous in ablation procedures where it is desired to precisely locate the ablation electrode for performing an ablation procedure. The steerable catheter makes it possible to accommodate many different situations, as for example small hearts, large hearts tortuous vessels and the like without the necessity of changing catheters. Also with the catheter of the present invention it is possible to retain the distal extremity of the catheter in a firm yieldable engagement with the wall of the heart while still making it possible to readily form bends in the distal extremity of the catheter.

What is claimed is:

1. A steerable catheter comprising a flexible elongate tubular member having proximal and distal extremities, a handle secured to the proximal extremity, said tubular member having a lumen extending therethrough, a mandrel slidably mounted in the lumen and extending into the distal extremity and means extending through the tubular member for causing bending of the distal extremity with respect to the mandrel disposed therein, said flexible elongate tubular member having an inner sleeve and an outer sleeve, said outer sleeve extending over the inner sleeve, one af said inner and outer sleeves between the proximal distal extremities of the flexible elongate tubular member being twisted through an angle of at least 250 degrees with respect to the other of said inner and outer sleeves and being secured to each other to inhibit whipping of the distal extremity of the flexible elongate tubular member as the handle is used to impart rotational movement of the flexible elongate tubular member.

2. A catheter as in claim 1 together with means carried by the handle for moving the mandrel longitudinally of the flexible elongate member to cause bends of different radii to be formed in the distal extremity of the flexible elongate tubular member, said mandrel including first and second members, slidably mounted with respect to each other and disposed in the distal extremity of the flexible elongate tubular member and having portions thereof overlapping each other and wherein said means carried by the handle for moving the mandrel longitudinally of the flexible elongate member includes means for changing the amount of overlap of the first and second members with respect to each other.

3. A device as in claim 2 wherein said means for causing bending of the distal extremity with respect to the mandrel consists of a pull wire secured to the distal extremity of the flexible elongate member and means carried by the handle for advancing and retracting the pull wire.

4. A catheter as in claim 3 wherein said mandrel includes Nitinol memory means carried by the distal extremity of the flexible elongate tubular member having a memory which wishes to assume a straight shape to aid in returning the distal extremity of the flexible elongate member to a straight shape when the pull wire is released.

5. A catheter as in claim 4 wherein said memory means assuming a straight shape is comprised of a superelastic material in ribbon-like form having a width and a thickness and solely permitting bending of the ribbon in a direction which is perpendicular to the surface forming the width of the ribbon.

6. A catheter as in claim 2 wherein the means carried by the handle for changing the amount of overlap of the portions includes a pin secured to the mandrel and a sleeve carried by the handle and rotatably mounted on the handle and means coupled to the sleeve and to the pin for causing longitudinal movement of the pin with respect to the handle upon rotation of the sleeve.

7. Steerable catheter as in claim 1 wherein the inner sleeve is twisted with respect to the outer sleeve.

8. A steerable catheter as in claim 7 wherein the outer sleeve is formed of materials which includes a braid.

9. A steerable catheter as in claim 8 wherein said braid includes a plurality of stainless steel strands.

10. A steerable catheter comprising a flexible elongate tubular member having proximal and distal extremities, a handle secured to the proximal extremity, said flexible elongate tubular member comprising an inner shaft having at least one lumen extending therethrough, a coaxial sleeve mounted on the shaft, at least a portion of said shaft having a twist provided therein and means for securing said sleeve to said shaft at opposite ends of said portion to retain said twist in said shaft, a pull wire extending through said at least one lumen and connected to the distal extremity of the flexible elongate tubular member and means carried by the handle and secured to the pull wire for retracting and advancing said pull wire, said sleeve being formed of a material having good torque transmitting properties, said pull wire being used for placing a bend in the distal extremity of the flexible elongate tubular member, said twist in said portion of said shaft serving to prevent the pull wire from selecting a preferred orientation when said portion of the shaft is formed into a bend.

11. A catheter as in claim 10 wherein said twist extends through substantially 360°.

12. A catheter as in claim 10 Wherein said portion of the shaft has a length of approximately 15".

13. A catheter as in claim 10 wherein said shaft is provided with a central lumen, a mandrel slidably mounted in said central lumen and extending to the distal extremity and means carried by the handle and secured to the mandrel for advancing and retracting the mandrel in the central lumen.

14. A catheter as in claim 13 wherein the at least one lumen for the pull wire is offset with respect to the central lumen.

15. A method for preventing whipping of the distal extremity of a steerable catheter as the steerable catheter is rotated when a bend has been placed in the distal extremity of the steerable catheter of the type which is provided with an elongate shaft and having a centrally disposed lumen therein extending therethrough and an additional lumen disposed therein offset from the centrally disposed lumen and a coaxially mounted sleeve mounted on said shaft comprising imparting a twist to at least a portion of the shaft and securing opposite sides of the portion of the shaft having the portion therein to the sleeve to retain the twist in the shaft and placing a pull wire in the additional lumen in the shaft and secured to the distal extremity.

16. A method as in claim 15 together with the step of positioning a mandrel within the central lumen adjusting the position of the mandrel to adjust the radius of the bend placed in the distal extremity of the catheter as the pull wire is retracted.

17. A method as in claim 15 together with the step of placing a member in the distal extremity of the catheter having a superelastic memory in the form of a straight shape so that when the pull wire is advanced, the distal extremity of the catheter assumes a straight shape under the urging of the superelastic memory member.

18. A method as in claim 17 together with the step of forming the member having a superelastic memory into the form of a ribbon having a width greater than the thickness and orienting the ribbon so that the distal extremity of the flexible elongate tubular member will only bend in a direction toward the pull wire which is perpendicular to the width of the ribbon.

19. A steerable catheter comprising a flexible elongate tubular member having proximal and distal extremities, a handle secured to the proximal, said tubular member having a lumen extending therethrough, a bend location mandrel slidably mounted in the lumen extending into the distal extremity of the flexible elongate tubular member, said bend location mandrel including first and second members slidably mounted with respect to each other and disposed in the distal extremity of the flexible elongate tubular member, said first and second members having portions overlapping each other, means extending from the handle to the distal extremity of the flexible elongate tubular member for causing bending of the distal extremity of the flexible elongate tubular member and means secured to the handle for changing the amount of overlap of the first and second members to thereby change the radius of the bend in the distal extremity of the flexible elongate tubular member.

20. A steerable catheter as in claim 19 wherein said first and second members are in the form of ribbon-like members which are rectangular in cross-section and having a width which is greater than the thickness so that they will only bend in the direction which is perpendicular to the width of the first and second members.

21. A steerable catheter as in claim 20 wherein said ribbon-like members are formed of a superelastic material and having a memory for causing first and second members to assume a straight shape.

22. A steerable catheter as in claim 19 wherein a tip is carried by the distal extremity of the flexible elongate tubular member, wherein said bend location mandrel includes a mandrel member circular in cross-section, wherein said first member is secured to the distal extremity of the mandrel member and wherein said second member is secured to said tip.

23. A method for adjusting the radius of the bend in the distal extremity of a steerable catheter, providing mandrel means having overlapping portions which is slidably mounted in the distal extremity of the catheter, providing pull wire means secured to the distal extremity of the catheter for creating a bend in the distal extremity of the catheter and changing the amount of overlap of the overlapping portions to change the radius of the bend in the distal extremity of the catheter.

* * * * *